United States Patent [19]
Gundlach et al.

[11] Patent Number: 5,527,162
[45] Date of Patent: Jun. 18, 1996

[54] SUCTION APPARATUS, OPERATED BY COMPRESSED AIR, FOR DRAWING OFF DUST-LADEN GASES

[75] Inventors: Hans-Werner Gundlach, Bremen; Friedrich Jacob, Lilienthal, both of Germany

[73] Assignee: BEGO Bremer Goldschlagerei Wilh. Herbst GmbH & Co., Bremen, Germany

[21] Appl. No.: 429,021

[22] Filed: Apr. 26, 1995

Related U.S. Application Data

[63] Continuation of Ser. No. 135,490, Oct. 13, 1993, abandoned.

[30] Foreign Application Priority Data

Oct. 14, 1992 [DE] Germany .......................... 42 34 538.3

[51] Int. Cl.⁶ ........................................................ F04F 5/42
[52] U.S. Cl. ............................. 417/171; 417/163; 417/46
[58] Field of Search ................................... 417/171, 163, 417/46

[56] References Cited

U.S. PATENT DOCUMENTS

| | | | |
|---|---|---|---|
| 1,517,467 | 12/1924 | Schmidt | 417/163 |
| 1,950,828 | 3/1934 | Thompson | 417/171 |
| 2,795,197 | 6/1957 | Laster et al. | 417/171 |
| 2,938,658 | 5/1960 | Foster | 417/171 |
| 3,063,223 | 11/1962 | Arbisi | 417/171 |
| 3,099,965 | 8/1963 | Regenscheit | |
| 4,057,365 | 11/1977 | Colmer | 417/44.1 |
| 4,227,863 | 10/1980 | Sommerer | 417/171 |
| 4,409,746 | 10/1983 | Beck | 417/171 |
| 4,817,688 | 4/1989 | Corniea | 141/140 |
| 5,173,030 | 12/1992 | Heimhard et al. | 417/163 |

FOREIGN PATENT DOCUMENTS

| | | | |
|---|---|---|---|
| 203017 | 2/1908 | Germany . | |
| 1250093 | 9/1967 | Germany . | |
| 2261297 | 6/1974 | Germany . | |
| 7244477 | 12/1976 | Germany . | |
| 3408812 | 7/1985 | Germany . | |
| 1732005 | 5/1992 | U.S.S.R. | 417/171 |
| 1593279 | 7/1981 | United Kingdom . | |
| 2119503 | 11/1983 | United Kingdom . | |

Primary Examiner—Richard A. Bertsch
Assistant Examiner—Ted Kim
Attorney, Agent, or Firm—Sughrue, Mion, Zinn, Macpeak & Seas

[57] ABSTRACT

An apparatus for drawing off dust-laden gases, especially in the art of dental technique, has a ring channel (15) which can be loaded with compressed air. The airstream which is provided by a compressed-air nozzle (26) performs an arcuate movement in the ring channel (15), whereby dust-laden gases are drawn in through an annular slit (22) and conveyed to an outlet channel (13). The apparatus is suitable for drawing off gases from containers. The apparatus serves for drawing off dust-laden air which is released when mixing solid substances, for example dental investment material, in a container (10).

9 Claims, 4 Drawing Sheets

5,527,162

SUCTION APPARATUS, OPERATED BY COMPRESSED AIR, FOR DRAWING OFF DUST-LADEN GASES

This is a continuation of application No. 08/135,490, filed Oct. 13, 1993, now abandoned.

BACKGROUND OF THE INVENTION

The invention relates to an apparatus for drawing off especially dust-laden gases.

Such apparatuses are employed, for example, in the art of dental technique. When mixing investment materials, for example, quartozose dusts are released which have proved to be hazardous to health. Therefore, these dusts have to be drawn off.

Known apparatuses of this kind comprise a suction apparatus driven by an electromotor which draws off the dust-laden gases and conveys them to a filter located thereafter which liberates the dust particles. The disadvantage in the known apparatus is that it is complicated, noisy and trouble-prone.

SUMMARY OF THE INVENTION

The invention is, therefore, based on the object of creating a simple apparatus for drawing off dust-laden gases which is, especially by avoiding movable parts, not susceptible to malfunction.

This object is attained by an apparatus in which, at least one compressed-air nozzle is used for drawing off the dust-laden gases. The compressed-air nozzle opens into a suction head that takes the form of a ring channel and creates therein an arcuate circumferential flow of compressed air. This flow of compressed air creates a vacuum inside of the suction head, which causes the suction effect on the dust-laden gases. The dust-laden gases are thus drawn in and reach the suction head via the circumferential inlet opening or via at least a circumferential row of a plurality of inlet openings. The provision of compressed air is unproblematic because it is available anyway in almost all dental laboratories.

In an embodiment of the invention the cross-section of the ring channel widens in the direction of flow of the stream of compressed air. In this manner, the ring channel has sufficient volume for accomodating the gases which are drawn in along the ring channel.

The ring channel has an (annular) slit on the inner side of its ring area through which the drawn in gases enter along the ring channel. The dimensions of the ring channel and of the (annular) slit, respectively, are adjusted to the pressure of the air flow provided by the compressed-air nozzle so that an optimum supply of dust-laden gases to the ring channel is ensured.

At the edge of a container in which the dust-laden gases are set free after mixing solid substances, the suction head or ring channel is preferably positioned in such a way that the gases rising in the container can pass through the (annular) slit of the ring channel without being hindered. For this purpose, the arrangement of the inner ring area of the ring channel is adjusted to the arrangement of the edge of the container, namely in such a way that the dimension of the opening formed by the ring channel is equal to the opening of the container.

In an advantageous embodiment of the invention the suction head or the ring channel comprises an outlet pipe connection with a compressed-air nozzle which increases the suction effection of the apparatus.

Further details of the invention relate to the constructive design of the apparatus. An exemplary embodiment of the apparatus according to the invention is explained in more detail below with reference to the drawings. In these:

Figure 1:
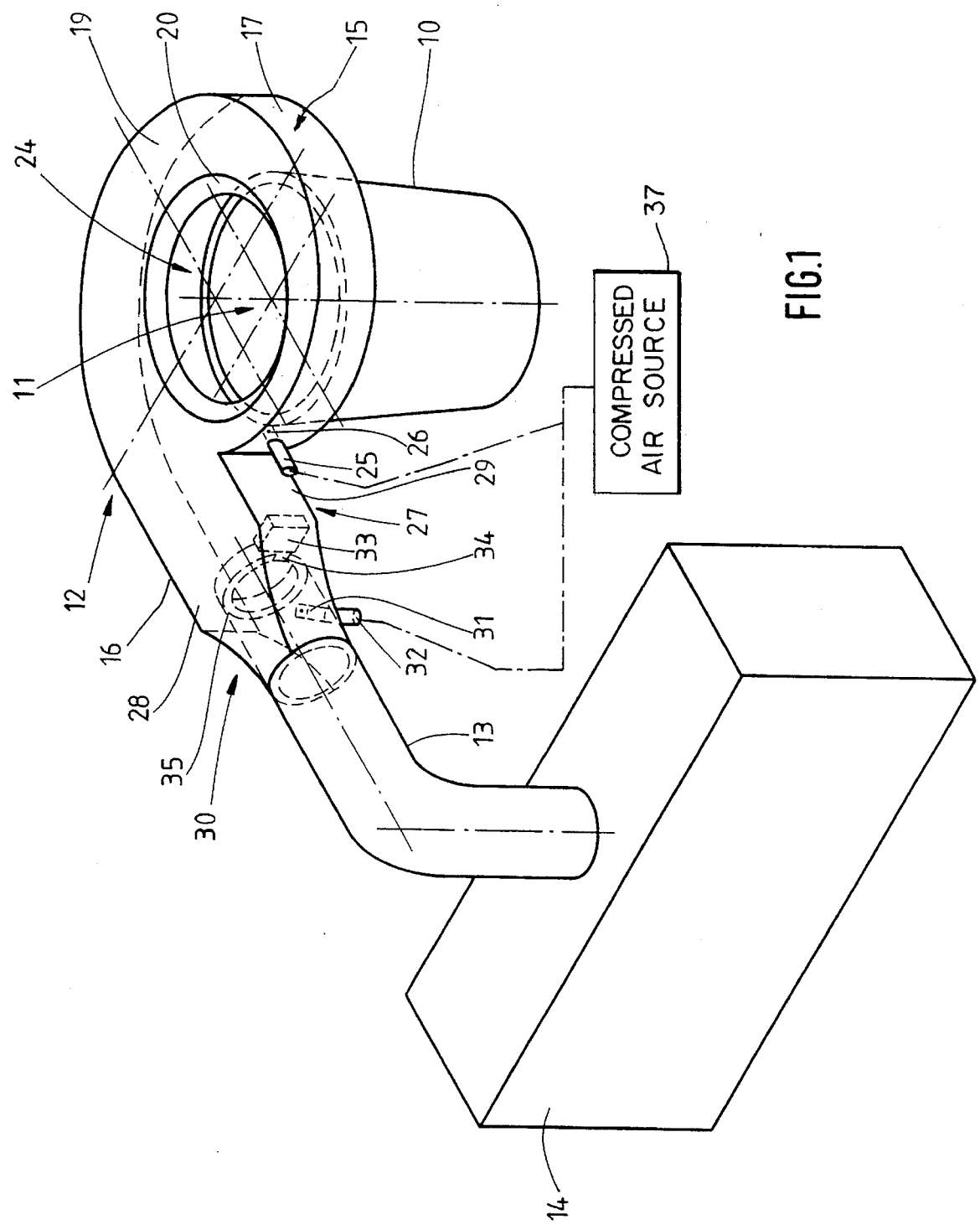
FIG. 1 shows a perspective view of an apparatus for drawing off gases.

The apparatus of the shown embodiment serves for drawing off health hazardous air which is released in the field of dental technique when processing investment material. In principle, however, the apparatus can also be employed in other fields.

The investment materials are mixed in a container 10, and the dust-laden air escapes through an opening 11 of the container 10. The suction head 12 is mounted on the upper edge of the container 10. The container 10 can thus be fed with the components for the investment material while the dust-laden air is drawn off. The apparatus comprises a suction head 12 which is connected to an outlet channel 13 which conveys the dust-laden air drawn in by the suction head 12 to a filter 14. This filter 14 serves for the liberation of the dust particles contained in the air. Instead of the filter 14 other dust separators may also be used.

Figure 3:
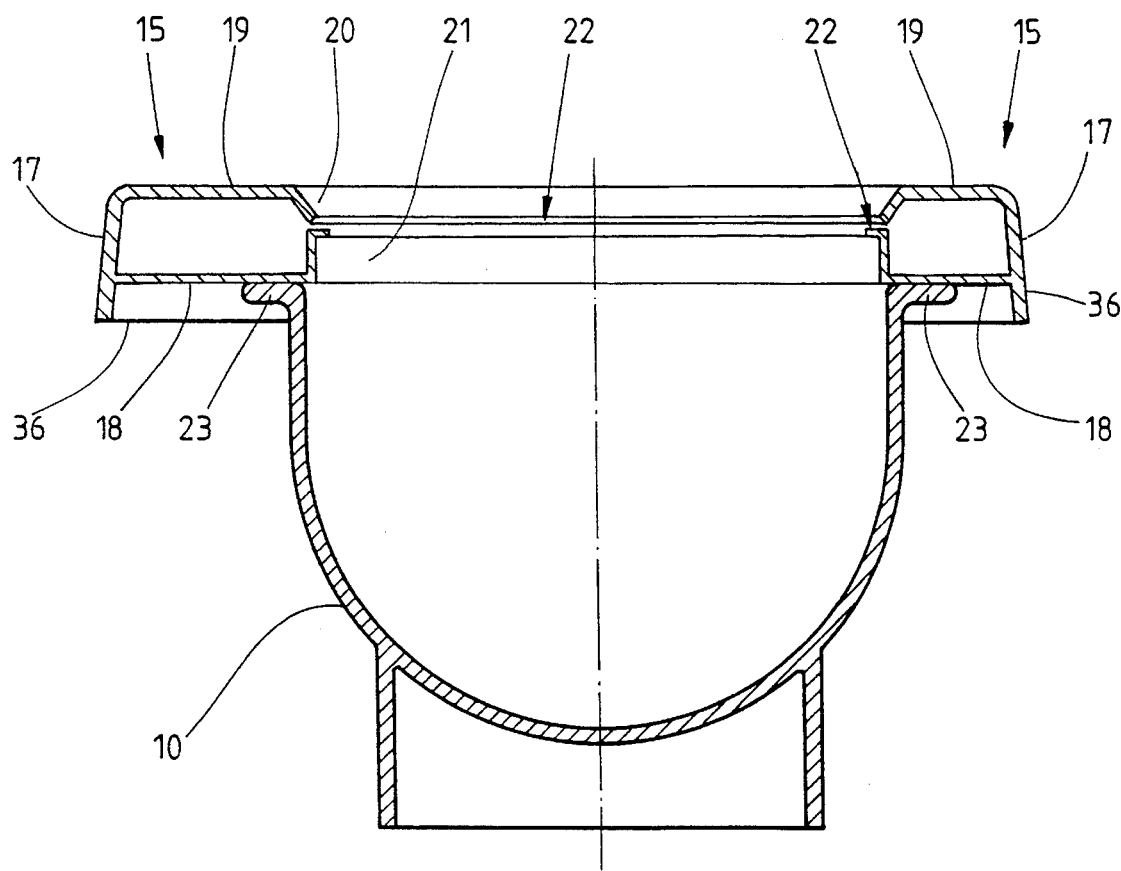
FIG. 3 shows a cross-section of a ring channel which is arranged on a container, taken along lines III—III in FIG. 2.
Figure 4:
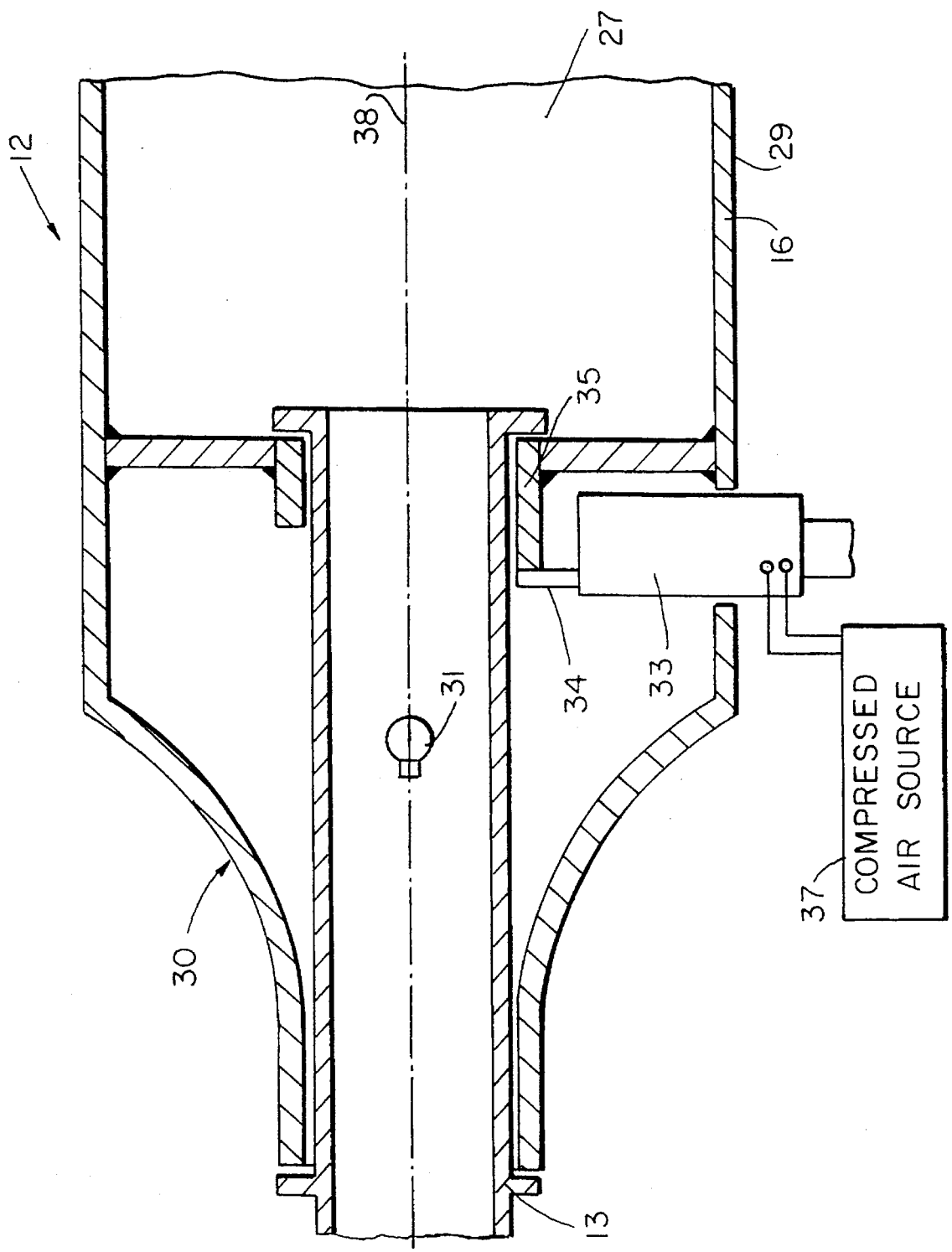
FIG. 4 shows a cross-section of the ring channel in the region of its connection with an outlet channel.

The suction head 12 comprises a ring channel 15 which accomodates the dust-laden gases and an outlet pipe connection 16 which discharges the gases. As can be seen particularly well in FIG. 3 the ring channel 15 comprises an upright outer wall 17, a horizontally extending bottom wall 18, a top wall 19, an upper inner wall extending in an inclined manner and a vertically extending lower inner wall 21. The upper inner wall adjoins the top wall 19 under an obtuse angle. Alternatively, the upper inner wall 20 can be arranged perpendicularly to the top wall 19. Between the upper inner wall 20 and the lower inner wall 21 a gap is formed which extends across the inner side of the ring channel 15 as a circumferential annular slit 22. Alternatively, it is also possible to provide a row of a plurality of individual bores.

In another embodiment the ring channel 15 can be formed exclusively from an upper inner wall 20 or a lower inner wall 21. The presence of the lower inner wall 22 is, however, not absolutely necessary for the functioning of the apparatus.

In the present example the suction head 12 has a circular opening 24 which approximately corresponds in its dimensions to the lateral opening 11 of the container 10. The ring channel 15 is mounted with its bottom wall 18 on the holding leg 23 on the edge of the container 10. The outer wall 17 is adjoined by a circumferential collar 36 which prevents the suction head 12 from slipping off the container 10. Separate fastening means may be used instead of the collar.

Figure 2:
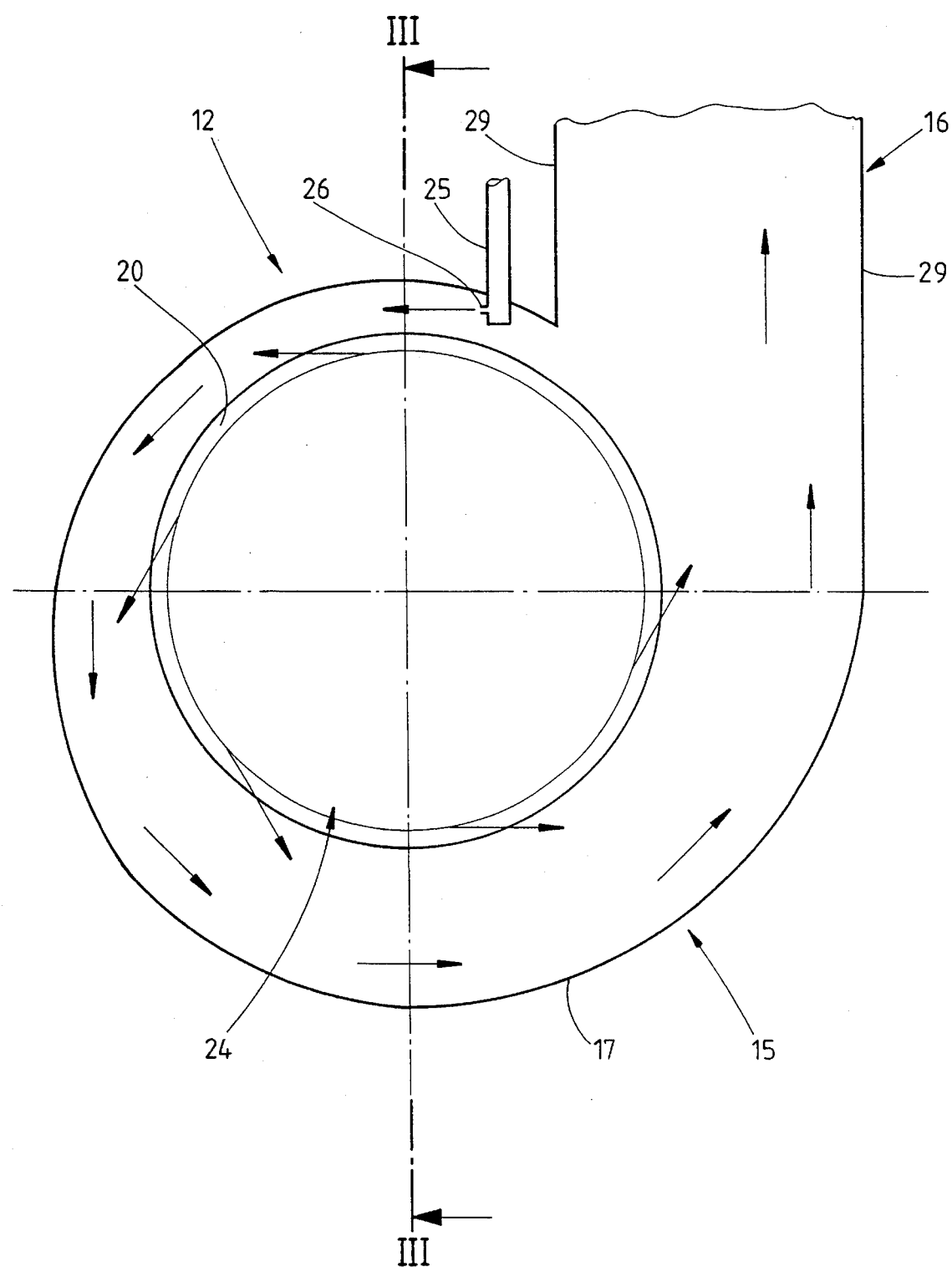
FIG. 2 shows a horizontal section of a ring channel.

As is evident particularly from FIG. 2, a pipe 25 is located in a bore of outer wall 17 of the ring channel and has a compressed-air nozzle 26 arranged at its free end pointing to the inside of the ring channel 15. The compressed-air nozzle 26 is arranged in such a manner that the compressed air emerging therefrom is injected into the ring channel approximately tangentially, that is in the longitudinal direction of the outer wall 17. The other end of the pipe which is arranged at the outside of the ring channel 15 is connected to a compressed-air source 37 by means of a compressed-air hose not shown.

The drawing off of the dust-laden gases inside and outside of the container is achieved in a way similar to the injector principle. The compressed air supplied by the compressed-air nozzle 26 is piped through the ring channel 15. Thereby, an arcuate circumferential flow of compressed air is created inside of the ring channel. As a result of the centripetal acceleration of the compressed air, a vacuum is created inside of the ring channel 15, namely in the region of the annular slit 22. The vacuum causes the gases in the region of the edge of the container 10 to be drawn in and to enter the ring channel 15 through the annular slit 22. The pressure of the stream of compressed air is such that the dust-laden gases are drawn in along the entire length of the ring channel 15.

In the present embodiment the ring channel 15 widens spirally in the direction of flow starting from the area where the compressed-air nozzle is located. For this purpose, the outer wall 17 of the ring channel 15 is circularly designed and extends away from the edge of the container 10 in the direction of flow. Because of the increase of diameter in the direction of flow, the ring channel 15 has sufficient cubic capacity to accomodate the volume of the air drawn in along the annular slit 22.

After the compressed-air stream carrying the drawn in dust-laden air has performed approximately one rotary movement around the edge of the container 10 inside the ring channel 15, it is drawn off in a straight line from the container 10 through the outlet pipe connection 16. For this purpose, the outlet pipe connection 16 adjoins a flat bottom wall 27, a top wall 28 and vertical side walls 29 which are arranged parallel to each other. The outlet pipe connection 16 tapers to the form of a tubular connection 30 until the diameter of the tubular connection 30 is equal to the diameter of the adjoining outlet channel 13.

To increase the suction effect a further compressed-air nozzle 31 is arranged at the inside of the outlet pipe connection 16, namely on the inside of the tubular connection 30. The outlet opening of this compressed-air nozzle is directed such that the compressed air that enters therefrom escapes in the direction of flow of the air. The stream of compressed air thereby extending in longitudinal dimension of the outlet pipe connection 16 has an effect similar to that of a steam ejector, and the tubular connection 30 decreases the cross-sectional area of the outlet pipe connection 16. Thereby, the suction effect of the suction head 12 is increased and the air is conveyed to the filter 14 with an increased pressure.

The compressed-air nozzle 31 and the compressed-air nozzle 26 are connected to the same compressed-air source 37 in the same manner. A pipe 32 of the compressed-air nozzle 31 extends through a bore in the top wall 28 of the outlet pipe connection 16. The outside end of the pipe 32 is connected to the compressed-air source 37 via a hose not shown in the drawings.

The suction head 12 is mounted pivotably (i.e. relatably in relation to the outlet channel 13. Thereby, pivoting the suction head 12 is possible so that free access to the container 10 is ensured. A limit switch 33 that is arranged at the inside of the outlet pipe connection 16 ensures that the supply of compressed air by the compressed-air nozzles 26 and 31 is interrupted or shut off if the suction head 12 is pivoted open. When in operation, a web 34 of the limit switch 33 is in contact with an annular insert 35 of the outlet pipe connection 16. The annular insert 35 is arranged axially in relation to the adjoining region of the outlet channel 13. By pivoting the suction head 12 about the horizontal longitudinal axis 38 of the outlet channel 13 the annular insert 35 is also moved, thereby interrupting the contact of the web 34 and the fixed limit switch 33 which causes the suction to be switched off. Instead of an electrical contact a mechanical switch would be possible, in which a web 34 biased with a spring is pushed down by the insert 35 while the suction head 12 is in operation.

What is claimed is:

1. In an apparatus for drawing off dust-laden gases, and comprising at least one suction head (12), the improvement wherein:

a) said suction head (12) has at least one inlet opening and one vacuum generator;

b) said suction head (12) has a ring channel (15) forming a circular opening (24) which corresponds to an upper circular opening (11) of a container (10);

c) said suction head (12) has an outlet pipe connection (16) which is arranged in a region of the largest cross-sectional area of the ring channel (15);

d) said suction head (12) is adjacent said upper circular opening (11) of the container (10) for treatment of investment material;

e) said vacuum generator comprises at least a first compressed-air nozzle (26) which opens into said suction head (12) and creates therein an arcuate circumferential flow of compressed air; and f) the cross-sectional area of said ring channel (15) increases steadily in the direction of said arcuate circumferential flow of said compressed air fed into said ring channel (15) by said compressed-air nozzle (26).

2. The apparatus of claim 1, wherein said ring channel (15) has a cylindrical inner wall (20, 21) which surrounds said circular opening (24) of said ring channel, and wherein said cylindrical inner wall (20, 21) of said ring channel (15) has only a single circumferential annular slit (22) forming said one inlet opening of said suction head (12).

3. The apparatus of claim 1, further comprising a second compressed air nozzle (31) in said suction head (12) in a region of said outlet pipe connection (16) of said suction head (12).

4. The apparatus of claim 3, wherein said suction head (12) is rotatably mounted on an outlet channel (13) which conveys the drawn-off dust-laden gases to a filter (14) along a common longitudinal axis of said outlet pipe connection and said outlet channel.

5. The apparatus of claim 4, further comprising a limit switch (33), disposed in said outlet pipe connection (16), for switching off a supply of compressed air when said suction head (12) is rotated.

6. The apparatus of claim 3 or 1, wherein said first compressed air nozzle (26) is located in a region of the smallest cross-sectional area of said ring channel.

7. In an apparatus for drawing off dust-laden gases, and comprising at least one suction head (12), the improvement wherein:

a) said suction head (12) has at least one inlet opening and one vacuum generator;

b) said suction head (12) is adjacent to an upper circular opening (11) of a container (10) for the treatment of investment material;

c) said suction head (12) comprises a ring channel (15) forming a circular opening (24) which corresponds to said circular opening (11) of said container (10);

d) said ring channel (15) and an outlet pipe connection (16) thereof are rotatably mounted on an outlet channel (13) of said suction head;

e) said vacuum generator has at least one compressed-air nozzle (26) opening into said suction head (12); and f) said apparatus further comprises a limit switch (33), disposed in said outlet pipe connection (16), for switching off a supply of compressed air when said suction head (12) is rotated.

8. In an apparatus for drawing off air which is dust-laden, comprising at least one suction head (12) having at least one inlet opening and one vacuum generator, the improvement wherein:

a) said vacuum generator comprises at least a first compressed-air nozzle (26) opening into said suction head (12) and connected to a supply of compressed air;

b) said suction head (12) rests on an upper circular opening (11) of a container (10) for treatment of investment material;

c) said suction head (12) has a ring channel (15) forming a circular opening (24) which corresponds to said circular opening (11) of said container (10);

d) said apparatus further comprises a second compressed air nozzle (31) in said suction head (12) in a region of an outlet pipe connection (16) of said suction head (12), wherein said ring channel has a varying cross-sectional area, and wherein said outlet pipe connection (16) is located in a region of the largest cross-sectional area of said ring channel (15);

e) said suction head (12) is rotatably mounted on an outlet channel (13) which conveys the drawn-off dust-laden gases to a filter (14) along a common longitudinal axis of said outlet pipe connection and said outlet channel; and f) said apparatus further comprises a limit switch (33), disposed in said outlet pipe connection (16), for switching off the supply of compressed air when said suction head (12) is rotated.

9. In an apparatus for drawing off air which is dust-laden, and comprising at least one suction head (12) having an inlet opening and a vacuum generator, the improvement wherein:

a) said vacuum generator comprises at least a first compressed-air nozzle (26) opening into said suction head (12) and connected to a supply of compressed air;

b) said suction head (12) comprises a ring channel (15) forming a circular opening (24);

c) said ring channel (15) has a cylindrical inner wall (20, 21) surrounding said circular opening (24);

d) said cylindrical inner wall (20, 21) of said ring channel (15) has only a single circumferential annular slit (22) forming said inlet opening of said suction head (12);

e) said apparatus further comprises a second compressed air nozzle (31) in said suction head (12) in a region of an outlet pipe connection (16) of said suction head (12), said ring channel has a varying cross-sectional area, and said outlet pipe connection (16) is located in a region of the largest cross-sectional area of said ring channel (15);

f) said suction head (12) is rotatably mounted on an outlet channel (13) which conveys the drawn-off dust-laden air to a filter (14) along a common longitudinal axis of an outlet pipe connection and said outlet channel; and g) said apparatus further comprises a limit switch (33), disposed in said outlet pipe connection (16), for switching off the supply of compressed air when said suction head (12) is rotated.

\* \* \* \* \*